United States Patent [19]

Fujisawa et al.

[11] 3,984,403

[45] Oct. 5, 1976

[54] ARGININE AND LYSINE SALTS OF ACID CEPHALOSPORINS

[75] Inventors: Hiroshi Fujisawa, Toyonaka; Hiroaki Okada, Suita; Yasumoto Miura, Ikeda; Masahiko Fujita, Suita; Tsugio Shimamoto, Takarazuka, all of Japan

[73] Assignee: Takeda Chemical Industries, Ltd., Osaka, Japan

[22] Filed: June 19, 1973

[21] Appl. No.: 371,531

[30] Foreign Application Priority Data

June 30, 1972 Japan.................................. 47-66076
Jan. 30, 1973 Japan.................................. 48-12631

[52] U.S. Cl............................. 260/243 C; 424/246
[51] Int. Cl.$^2$...................................... C07D 501/60
[58] Field of Search ................................. 260/243 C

[56] References Cited
UNITED STATES PATENTS

| | | |
|---|---|---|
| 3,280,118 | 10/1966 | Fardley et al. ................. 260/243 C |
| 3,488,730 | 1/1970 | Stephens ........................ 260/243 C |
| 3,676,434 | 7/1972 | Massey........................... 260/243 C |
| 3,708,478 | 1/1973 | Chapman et al................ 260/243 C |

*Primary Examiner*—Nicholas S. Rizzo
*Assistant Examiner*—Jose Tovar
*Attorney, Agent, or Firm*—Wenderoth, Lind & Ponack

[57] ABSTRACT

Arginine or lysine salt of acid cephalosporins can be administered parenterally, e.g., by intramuscular injection, with no substantial pain. Preferred acid cephalosporin salts are l-arginine or lysine salts of N-[7-(α-sulfophenylacetamido)ceph-3-em-3-ylmethyl]-pyridinium-4-carboxylate, N-[7-(α-sulfophenylacetamido)-ceph-3-em-3-ylmethyl]-(4'-carbamoyl)pyridinium 4-carboxylate, 7-cyanoacetamido-cephalosporanic acid, 7-(2'-thienylacetamido)-3-[6''-(3''-methylpyridazinyl)thiomethyl]-ceph-3-em-4-carboxylic acid 2''-oxide, 7-tetrazolylacetamido-3-[5'-(2'-methylthiadiazolyl)thiomethyl]-ceph-3-em-4-carboxylic acid and 7-(2'-thienylacetamido)-cephalosporanic acid.

11 Claims, No Drawings

ARGININE AND LYSINE SALTS OF ACID CEPHALOSPORINS

The present invention relates to new salts of cephalosporins, more particularly arginine and lysine salts of acid cephalosporins, to their preparation and to their use in pharmaceutical compositions. It is known that when injected intramuscularly or subcutaneously, acid cephalosporins generally cause local reactions (e.g., pain, reddening, induration, swelling, etc., at the site of injection), both during and following the injection. To reduce the pain, local anaesthetics, e.g., procaine hydrochloride, lidocaine hydrochloride, benzyl alcohol, etc., are sometimes added to the solution to be injected. However, the local anaesthetics hardly reduce the delayed pain following the injection, although they can reduce the immediate pain almost satisfactorily.

In search of acid cephalosporins which would be free from the above disadvantage, we conducted extensive research and ultimately discovered that arginine and lysine salts of these cephalosporins are not only free from the above disadvantage but have other desirable qualities without sacrificing their antibacterial activity. One of the desirable qualities is higher stability, other advantages being an enhanced degree of solubility and an increased rate of dissolution in water at room temperature as compared with the corresponding sodium salts. This invention is the culmination of the above discovery.

The term "acid cephalosporin" as used in the context of this invention means any and all cephalosporins which contain one or more free acid radicals, such as carboxyl, sulfo, etc., within the respective molecules or which may be converted to alkali or alkaline earth metal salts with such elements as sodium, potassium, calcium and the like. Therefore, the 7-acyl groups of such acid cephalosporins may be any of aliphatic carboxylic acid acyl groups such as acetyl, propionoyl, hexanoyl, heptanoyl, octanoyl, cyclopentanoyl, etc.; mono-substituted aliphatic carboxylic acid acyl groups such as phenylacetyl, cyclohexylacetyl, 1-cyclohexenylacetyl, 1,4-cyclohexadienylacetyl, phenoxybutyloyl, nitrophenylacetyl, phenylpropionyl, butylthioacetyl, phenylthioacetyl, chlorophenylthioacetyl, benzylthioacetyl, phenethylthioacetyl, allylthioacetyl, 4-pyridylthioacetyl, benzylthiopropionyl, (1-imino-2-phenylethyl)aminoacetyl, 2-(3-sydnon)acetyl, 1-pyrazolylacetyl, 4-nitro-1-pyrazolylacetyl, 4-chloro-1-pyrazolylacetyl, 3,5-dimethyl-1-pyrazolylacetyl, 2-furylacetyl, 6-(2'-oxo-3'-methylpyridazinyl)thioacetyl, etc.; di-substituted aliphatic carboxylic acid acyl groups such as α-carboxylphenylacetyl, α-bromopropionyl, α-aminophenylacetyl, α-hydroxyphenylacetyl, α-sulfophenylacetyl, α-sulfo-(p-aminophenyl)acetyl, α-phenoxypropionyl, α-phenoxybutyloyl, phenylglycyl, 1-cyclohexenylglycyl, thienylglycyl, furylglycyl, cyclohexdienylglycyl, phenylmethylglycyl, carbamoylphenylacetyl, 5-amino-5-carboxyvaleryl, 5-carboxy-5-(2',6'-dialkyl-3',5'-dicarboalkoxy-1',4'-dihydropyrido-1'-yl)valeryl, etc.; acryl; aromatic acyl groups such as benzoyl, 2,6-dimethoxybenzoyl, etc.; heterocyclic acyl groups such as 5-methyl-3-phenyl-4-isoxazolylcarbonyl, 3-o-chlorophenyl-5-methyl-4-isoxazolylcarbonyl, 3-(2,6-dichlorophenyl)-5-methyl-4-isoxazolylcarbonyl, etc.; and so forth. When such acyl groups have an amino group, the amino group may be previously protected with a protective substituent such as carbobenzoxy, phthalyl, phenylthiocarbonyl, methylsulfonylethoxycarbonyl, isobornyloxycarbonyl, benzyloxycarbonyl and the like. Further, the 7-position of the cephem nucleus may have such substituents as, for example, an alkoxy group, e.g., methoxy, ethoxy, etc.; an acyloxy group, e.g., acetyloxy. The acetoxymethyl group in the 3-position or the acetoxy moiety of said acetoxymethyl group may be previously converted to hydrogen; hydroxyl; an alkoxy group, e.g., methoxy or ethoxy; mercapto, an alkyl-substituted mercapto group such as a mercapto group substituted by methyl, ethyl, propyl or pentyl; an aryl-substituted mercapto group such as one substituted by phenyl, p-nitrophenyl, tolyl or naphthyl; a mercapto group substituted by a heterocyclic group such as pyridyl, 1-oxopyridyl, pyrimidyl, 2-oxopyrimidyl, 2-thionepyrimidyl, 2-oxo-5-methylpyrimidyl, pyridazinyl, 1 or 2-oxopyridazinyl, thienyl, pyrazolyl, diazolyl, triazolyl, tetrazolyl, oxadiazolyl, thiadiazolyl, 5-methyl-1,3,4-thiadiazol-2-yl, 5'-methyl-1',3',4'-thiadiazolyl, 6-oxopurinyl or uracil; a mercapto group substituted by a substituted thiocarbonyl group such as acetylthiocarbonyl or N-methylpiperazinothiocarbonyl; an acyloxy group such as propoxy or carbamoyloxy; pyrimidinium; 4-carbamoylpyridinium; imidazolium; azo; amino; a substituted amino group such as methylamino or diethylamino; or the like. Preferable acid cephalosporins employed may be illustrated by the general formula:

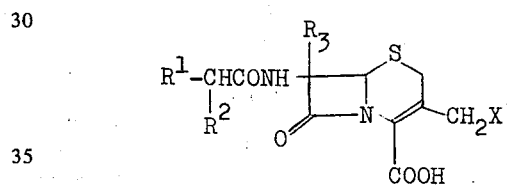

wherein $R^1$ represents phenyl, 2-thienyl, phenoxy, 1-cyclohexenyl, tetrazolyl, cyano, 4-pyridylthio, phenylthio, (1'-imino-2'-phenylethyl)amino or 2-(3-sydnon) group, $R^2$ represents hydrogen, sulfo, carboxyl, amino, methyl or ethyl group, $R^3$ represents hydrogen or methoxy group and X represents hydrogen, acetoxy, alkoxy, substituted thio or tertiary-ammonium group. Thus, specific examples of said acid cephalosporin include 7-cyanoacetamido-cephalosporanic acid, N-[7-(α-sulfophenylacetamido)ceph-3-em-3-ylmethyl]-pyridinium-4-carboxylate, N-[7-(α-sulfophenylacetamido)ceph-3-em-3-ylmethyl]-(4-carbamoyl)pyridinium-4-carboxylate, 7-(2'-thienylacetamido)-3-[6''-(3''-methylpyridazinyl)thiomethyl]-ceph-3-em-4-carboxylic acid 2''-oxide, 7-tetrazolylacetamido-3-[5'-(2'-methylthiadiazolyl)thiomethyl]-ceph-3-em-4-carboxylic acid, 7-(α-aminophenylacetamido)-3-methyl ceph-3-em-4-carboxylic acid, 7-cyanoacetamido-cephalosporanic acid, 7-(4-pyridylthioacetamido)cephalosporanic acid, 7-(2-thienylacetamido)-7-methoxy-3-carbamoyloxymethyl-ceph-3-em-4-carboxylic acid, 7-(1-imino-2-phenylethyl)aminoacetamido-3-[5'-2'-methylthiadiazolyl)thiomethyl]-ceph-3-em-4-carboxylic acid, 3-(5-methyl-1,3,4-thiadiazol-2-ylthiomethyl)-7-[2-(3-sydnon)acetamido]-ceph-3-em-4-carboxylic acid, and so forth.

Arginine or lysine, another component of the salts, may be in any form of the d,l and dl-form, but l-form is most preferable. These compounds are substantially non-toxic. Thus, the new salts of the present invention may be given in a large dose and over a rather long time.

The new salts of the present invention may be prepared in a per se known method and the reaction conditions may be varied within a wide range.

The acid cephalosporin part or arginine or lysine part of the salts may be used in the free form or their suitable salts. The reaction is carried out in a solvent or in a homogenous or heterogenous solvent mixture, in which the reagents are soluble. The reactions are desirably carried out in the presence of water, a water-miscible organic solvent, a water-immiscible organic solvent or a mixture thereof, as required. Preferably the two reactants are reacted in approximately equivalent proportions. The reaction is desirably conducted at or below room temperature.

The reaction can be practiced by, for example, reacting an acid cephalosporin with arginine or lysine; reacting a basic salt of an acid cephalosporin (e.g., barium, magnesium or other salt) with an acid salt of arginine or lysine (e.g., sulfate or phosphate); passing a salt of arginine or lysine over a basic ion exchange resin (e.g., Amberlite IRA-411, Rohm and Haas Co., U.S.A.) and reacting the resultant free base with an acid cephalosporin; rendering a salt of an acid cephalosporin acidic with hydrochloric acid, extracting the acid cephalosporin with an organic solvent (e.g., ethyl acetate) and reacting the same with arginine or lysine; or adsorbing arginine or lysine or a salt thereof on a strongly acid ion exchange resin (e.g., Amberlite IR-120, Rohm and Haas Co., U.S.A.) and passing a salt of an acid cephalosporin through the resin to effect an exchange reaction.

The reaction product thus obtained may if required be purified and concentrated and, then, the desired compound can be isolated by such procedures as lyophilization, spray drying or the dropwise addition of a water-miscible organic solvent (e.g., dioxane or acetone). The salts may be isolated either as precipitates formed spontaneously or by the addition of a suitable chemical agent. Another way of isolating the salt, in case it is prepared from an approximately equivalent amount of the free arginine or lysine with a free acid cephalosporin employed, is to remove a solvent, e.g., water or a solvent mixture at a temperature above or below the freezing point of the reaction mixture.

The resultant acid cephalosporin arginine or lysine salt can be formulated into injections in the conventional manner. The injections may be prepared from the isolated salt or in some instances from the reaction mixture itself containing the salt in an aqueous solution provided that the reaction mixture does not contain large amounts of by-products. The injections may contain, in addition to the salt, smaller amounts of additives, e.g., to give them a desirable pH-value or storage stability, etc.

The salts of the present invention are used as injections, usually at daily dosage of 0.1 to 7 g. in general for adults. For example, 7-tetrazolylacetamido-3-[5'-(2'-methylthiazolyl)thiomethyl]-ceph-3-em-4-carboxylic acid l-arginine salt: an aqueous solution containing 0.5 to 6 grams; N-[7-(α-sulfophenylacetamido)-ceph-3-em-3-ylmethyl]-pyridinium-4-carboxylate l-arginine salt: an aqueous solution containing 1 to 6 grams; and 7-(2'-thienylacetamido)-3[6''-(3''-methyl-pyridazinyl)-thiomethyl]3-em-4-carboxylic acid 2''-oxide l-arginine salt: an aqueous solution containing 0.1 to 5 grams.

Table 1 shows the results obtained when 7-(2'-thienylacetamido)cephalosporanic acid (hereafter referred to briefly as "CET")-sodium salt, CET-arginine salt and CET-lysine salt are respectively administered at the dose of 2 ml in the concentration of 200 mg. (potency)/ml. It will be seen from Table 1 that, in sharp contrast to CET sodium salt, the intramuscular administration of CET-arginine and lysine salts produces substantially no pain in human subjects.

Table 1

| CET salt | Number of cases | Observation |
| --- | --- | --- |
| CET-sodium | 2 | A severe pain at the time of injection; the pain increases with time and lasts for 10 to 30 minutes. |
| CET-lysine | 4 | No pain at the time of injection; substantially no pain is felt thereafter. |
| CET-arginine | 4 | No pain at the time of injection; a slight pain is felt thereafter. |

The pain test described in Table 2 was performed as follows. The various salts of 7-(2'-thienylacetamido)-3-[6''-(3''-methylpyridazinyl)thiomethyl]-3-cephem-4-carboxylic acid 2''-oxide (hereafter referred to briefly as "TPO") were respectively dissolved in distilled water for injection at the rate of 250 mg. (potency)ml, and two different salt solutions were intramuscularly injected into the deltoid muscles of human subjects at a dose of 1 ml each in a pair scheme by the double blind test method.

Generally the pain of injection is considerably influenced by the concentration of the medicament, pH and osmotic pressure of the injection. In this pain test, notwithstanding the fact that the above conditions were substantially identical, the pain which accompanied the injection of the l-arginine salt and l-lysine salt of thienylcephem compound was considerably less pronounced than the pain which accompanied the administration of the corresponding sodium salt.

Table 2

| TPO salt | Number of cases | Pain at the time of injection* | Remarks |
| --- | --- | --- | --- |
| TPO-sodium | 4 | +++ | A severe pain during and after injection |
| TPO-lysine | 4 | ± | A slight pain during and after injection |
| TPO-arginine | 8 | ± | A slight pain during and after injection |

*—: Substantially no pain ±: Hint of pain +: Slight pain ++: Appreciable pain +++: Severe pain The pain test of N-[7-(α-sulfophenylacetamido)-ceph-3-em-3-ylmethyl]-(4-carbamoyl)pyridinium-4-carboxylate salt is carried out in the same manner as the pain test of TPO described above. The results are shown in Table 3.

Table 3

| Salt | Number of Cases | Pain at the time of injection* | Remarks |
|---|---|---|---|
| Sodium salt | 4 | +++ | A severe pain during and after injection |
| l-Lysine salt | 4 | ± | A slight pain during and after injection |
| l-Arginine salt | 4 | ± | A slight pain during and after injection |

*Symbols mean the same as in Table 2.

It is to be understood that the following examples are solely for the purpose of illustration and not to be construed as limitative of this invention, and that many variations may be resorted to without departing from the spirit and scope of this invention. In this specification, g., mg., mcg., ml, cm, decomp., Calcd., vs, s, m and w are "gram", "milligram", "microgram", "milliliter", "centimeter", "decomposed", "Calculated", "very strong", "strong", "medium" and "weak", respectively. Temperatures are all uncorrected, and percentages are all on the weight basis. Potencies of the object compounds in the following examples are calculated by employing the corresponding free compounds as the control.

EXAMPLE 1

In 10 ml. of water is suspended 1.00 g. of CET and, under stirring, 0.44 g. of l-arginine is gradually added. The reaction yields a pale yellowish clear aqueous solution. This solution is aseptically filtered and lyophilized to obtain a pale yellowish product of CET-l-arginine salt. Yield 98%; Melting point 143°–146°C(decomp.)

UV absorbance ratio $E_{265}/E_{237} = 0.60$. Nitrogen content 14.73 % (calcd.); 14.10 % (found). Antibiotic potency 685 mcg. (potency)/mg. IR spectrum: $\nu^{KBr}_{max}$ (cm$^{-1}$): 3350(w), 3140(w), 1750(s), 1720(s), 1680(s), 1650(vs), 1610(vs), 1510(m).

EXAMPLE 2

In 10 ml of water is suspended 1.00 g. of CET. In the meantime, l-lysine hydrochloride is dissolved in water and the solution is passed over a basic ion exchange resin (Amberlite IRA-411 of Rohm and Haas Co., U.S.A.). The aqueous solution of free l-lysine base thus obtained (containing 0.37 g. of l-lysine) is added to the above suspension. The resultant pale-yellowish solution is lyophilized, whereupon a porous solid product is obtained. This product is recrystallized from a solvent mixture of water and ethanol to harvest crystalline CET-l-lysine salt. Yield: 70%.

Melting point: 150°–153°C(decomp.). Nitrogen content: 10.32 % (calcd.); 10.55 % (found). Antibiotic potency: 738 mgc.(potency)/mg. UV absorbance ratio: $E_{265}/E_{237} = 0.60$.

EXAMPLE 3

In 15 ml. of water is suspended 3.824 g. of TPO and, under cooling with ice and stirring, a solution of 1.393 g. l-arginine in 5 ml, water is added dropwise. The mixture is stirred for about 15 minutes, whereby TPO is completely dissolved to give a clear solution. The solution is filtered once and 300 ml. of ethanol is added to the filtrate. The resultant precipitate is recovered and dissolved in 10 ml. of water, followed by lyophilization. The procedure yields 2.710 g. of TPO-arginine salt.

Melting point: 163°–173°C(decomp.) Analysis ($C_{25}H_{32}O_7N_8S_3.2H_2O$): Calcd. C, 43.59; H, 5.26; N, 16.26. Found C, 43.84; H, 4.89; N, 16.06. IR spectrum: $\nu^{KBr}_{max}$ (cm$^{-1}$): 3400(vs), 1760(s), 1690(s), 1630(vs), 1610(vs), 1530(s).

EXAMPLE 4

In 15 ml. of water is suspended 3.824 g. of TPO and, under cooling with ice and stirring, a solution of 1.168 g. l-lysine in 5 ml. water is added dropwise. Thereafter, the reaction mixture is treated in the same manner as Example 3 to obtain 2.22 g. of TPO-lysine salt.

Melting point: 167°–171°C(decomp.). Analysis ($C_{25}H_{32}O_7N_6S_3.2H_2O$): Calcd. C, 45.44; H, 5.49; N, 12.71. Found C, 45.26; H, 5.00; N, 12.59. IR spectrum: $\nu^{KBr}_{max}$(cm$^{-1}$): 3430(vs), 1765(s), 1690(s), 1610(vs), 1540(s).

EXAMPLE 5

In 10 ml. of distilled water is suspended 1.0 g. of free 7-cyanoacetamido-cephalosporanic acid and the solution is cooled to about 5°C with vigorous stirring. An aqueous solution containing 0.431 g. of l-lysine is added dropwise to the above suspension, whereby the free 7-cyanoacetamidocephalosporanic acid is dissolved. The solution is filtered under suction and the filtrate is lyophilized. The lyophilizate is dissolved in a small amount of water, to which ethanol is added dropwise to precipitate l-lysine salt of 7-cyanoacetamidocephalosporanic acid. Yield 80 %, Melting point: 133°–135°C(decomp.). Nitrogen content: 14.42 % (calcd.) 14.53 % (found) Antibiotic potency 695 mcg.(potency)/mg. IR spectrum: $\nu^{KBr}_{max}$ (cm$^{-1}$): 3400(m), 2240(w), 1750(vs), 1670(s), 1610(vs), 1540(s), 1230(s).

EXAMPLE 6

In 10 ml. of distilled water is dissolved 1.0 g. of N-[7-(α-sulfophenylacetamido)ceph-3-em-3-ylmethyl]-pyridinium-4-carboxylate sodium salt and the solution is passed over an ion exchange resin (Amberlite IR-120 of Rohm and Haas Co., U.S.A.) to obtain an aqueous solution of free acid N-[7-(α-sulfophenylacetamido)-ceph-3-em-3-ylmethyl]pyridinium-4-carboxylate.

While the solution is cooled, 0.341 g. of l-arginine is added and after its pH is adjusted to 5, the solution is aseptically filtered and lyophilized.

Yield 98 %. Nitrogen content: 14.77 % (calcd.); 14.89 % (found). Antibiotic potency 721 mcg.(potency)/mg.

EXAMPLE 7

In 10 ml. of water is suspended 1.000 g. of 7-tetrazolylacetamido-3-[5'-(2'-methylthiazolyl)thiomethyl]-3-cephem-4-carboxylic acid and, under cooling with ice and stirring, 1 ml. of an aqueous solution containing 0.509 g. of l-arginine is added dropwise, whereupon the 7-tetrazolylacetamido-3-[5'-(2'-methylthiazolyl)-thiomethyl]-3-cephem-4-carboxylic acid is completely dissolved. The solution is aseptically filtered and lyophilized, whereupon pale-yellowish white 7-tetrazolylacetamido-3-[5'-(2'-methylthiazolyl)thiomethyl]-3-cephem-4-carboxylic acid salt of arginine is obtained.

Nitrogen content: 32.53 % (calcd.); 31.98 % (found). Antibiotic potency: 658 mcg.(potency)/mg. Yield: 95 %.

EXAMPLE 8

In 5 ml. of distilled water is dissolved 1.0 g. of N-[7-(α-sulfophenylacetamido)ceph-3-em-3-ylmethyl]-(4-carbamoyl)pyridinium-4-carboxylate sodium salt and, under cooling at about 5°C, the solution is passed over an ion exchange resin (Amberlite IR-120 of Rohm and Haas Co., U.S.A.) to obtain an aqueous solution of the free acid. To this solution is added an aqueous solution containing 0.315 g. of free l-lysine base which has been prepared by means of a basic ion exchange resin (Amberlite IRA-411 of Rohm and Haas Co., U.S.A.). The reaction mixture is aseptically filtered and lyophilized. Yield 94 %.

Nitrogen content: 12.38 % (calcd.); 12.53 % (found). Antibiotic potency 768 mcg.(potency)/mg. IR spectrum: $\nu^{KBr}{}_{max}$(cm$^{-1}$): 3330(s), 1760(s), 1610(vs), 1390(s), 1200(m), 1180(m).

EXAMPLE 9

In a manner similar to Example 8, l-arginine salt of N-[7-(α-sulfophenylacetamido)ceph-3-em-3-ylmethyl]-(4-carbamoyl)pyridinium-4-carboxylate is prepared. Yield 93 %.

Nitrogen content: 15.85 % (calcd.); 15.98 % (found). Antibiotic potency 735 mcg(potency)/mg. IR spectrum: $\nu^{KBr}{}_{max}$(cm$^{-1}$): 3330(s), 1760(s), 1610(vs), 1390(s), 1200(m), 1180(m).

What is claimed is:

1. A salt of an acid cephalosporin with arginine or lysine, wherein the acid cephalosporin has the formula

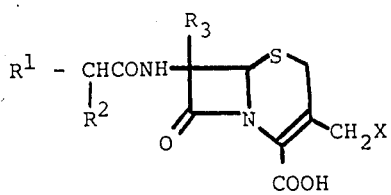

wherein R$^1$ represents phenyl, 2-thienyl, phenoxy, 1-cyclohexenyl, tetrazolyl, cyano, 4-pyridylthio, phenylthio, (1'-imino-2'-phenylethyl)amino or 2-(3-sydnon), R$^2$ represents hydrogen, sulfo, carboxyl, amino, methyl or ethyl, R$^3$ represents hydrogen or methoxy and X represents hydrogen, acetoxy, pyridyl, (4-carbamoyl) pyridyl, 6-(3-methylpyridazinyl-2-oxido) thio or 5-(2-methylthiadiazolyl) thio.

2. A salt as calimed in claim 1, wherein the acid cephalosporin is N-[7-(α-sulfophenylacetamido)ceph-3-em-3-ylmethyl]-pyridinium-4-carboxylate.

3. A salt as claimed in claim 1, wherein the acid cephalosporin is N-[7-(α-sulfophenylacetamido)ceph-3-em-3-ylmethyl]-(4'-carbamoyl)pyridinium-4-carboxylate.

4. A salt as claimed in claim 1, wherein the acid cephalosporin is 7-cyanoacetamido-cephalosporanic acid.

5. A salt as claimed in claim 1, wherein the acid cephalosporin is 7-(2'-thienylacetamido)-3-[6''-(3''-methylpyridazinyl)thiomethyl]-ceph-3-em-4-carboxylic acid 2''-oxide.

6. A salt as claimed in claim 1, wherein the acid cephalosporin is 7-tetrazolylacetamido-3-[5'-(2'-methylthiadiazolyl)thiomethyl]-3-cephem-4-carboxylic acid.

7. A salt as claimed in claim 1, wherein the acid cephalosporin is 7-(2'-thienylacetamido)cephalosporanic acid.

8. A salt as claimed in claim 1, wherein the arginine and lysine are of the l-form.

9. A salt as claimed in claim 1, wherein the arginine and lysine are of the dl-form.

10. A salt as claimed in claim 1, wherein the acid cephalosporin is 7-(α-aminophenyl acetamido)-3-methylceph-3-em-4-carboxylic acid.

11. A salt as claimed in claim 1, wherein the lysine is of the l-form.

* * * * *